United States Patent [19]
Oppelt et al.

[11] Patent Number: 5,435,304
[45] Date of Patent: Jul. 25, 1995

[54] METHOD AND APPARATUS FOR THERAPEUTIC TREATMENT WITH FOCUSSED ACOUSTIC WAVES SWITCHABLE BETWEEN A LOCATING MODE AND A THERAPY MODE

[75] Inventors: Sylvester Oppelt, Memmelsdorf; Arnim Rohwedder, Fuerth, both of Germany

[73] Assignee: Siemens Aktiengesellschaft, Munich, Germany

[21] Appl. No.: 36,231

[22] Filed: Mar. 24, 1993

[30] Foreign Application Priority Data

Apr. 24, 1992 [DE] Germany .......... 42 13 586.9

[51] Int. Cl.⁶ .............................. A61B 17/22
[52] U.S. Cl. ...................... 128/660.03; 601/4
[58] Field of Search ........ 128/24 EL, 24 AA, 660.03; 601/1, 2, 3, 4, 24 AA, 24 EL

[56] References Cited

U.S. PATENT DOCUMENTS

| | | |
|---|---|---|
| 3,237,623 | 3/1966 | Gordon . |
| 3,958,559 | 5/1976 | Glenn et al. . |
| 4,526,168 | 7/1985 | Hassler et al. . |
| 4,674,505 | 6/1987 | Pauli et al. . |
| 4,725,989 | 2/1988 | Granz et al. . |
| 4,821,730 | 4/1989 | Wurster et al. . |
| 4,928,671 | 5/1990 | Reichenberg et al. . |
| 5,009,232 | 4/1991 | Hassler et al. . |
| 5,076,277 | 12/1991 | Iwama et al. .............. 128/24 EL |
| 5,078,143 | 1/1992 | Okazaki et al. ............ 128/24 EL |
| 5,109,338 | 4/1992 | Ermert et al. ............. 128/24 EL |
| 5,215,091 | 6/1993 | Ishida ..................... 128/660.03 |
| 5,241,962 | 9/1993 | Iwama et al. .............. 128/660.03 |
| 5,243,985 | 9/1993 | Anda et al. ............... 128/660.03 |

FOREIGN PATENT DOCUMENTS

| | | |
|---|---|---|
| 0387858 | 3/1990 | European Pat. Off. . |
| 2722252 | 11/1978 | Germany . |
| 3328039 | 2/1985 | Germany . |
| 2187840 | 9/1987 | United Kingdom . |

OTHER PUBLICATIONS

"Kompendium Elektromedizin," Pätzold (1982) pp. 243–249.

*Primary Examiner*—K. M. Pfaffle
*Attorney, Agent, or Firm*—Hill, Steadman & Simpson

[57] ABSTRACT

A therapy apparatus for treatment with focused acoustic waves which has a source of focused acoustic waves, an acoustic receiver for the reception of parts of the acoustic waves reflected from a subject to be acoustically irradiated, and can be switched from a therapy mode to a locating mode. The apparatus also include circuitry for varying the oscillatory frequency of the generated acoustic waves dependent on whether the apparatus is switched to the therapy or locating mode. A method for operating such an apparatus is also disclosed.

20 Claims, 4 Drawing Sheets

METHOD AND APPARATUS FOR THERAPEUTIC TREATMENT WITH FOCUSSED ACOUSTIC WAVES SWITCHABLE BETWEEN A LOCATING MODE AND A THERAPY MODE

BACKGROUND OF THE INVENTION

1. Field of the Invention

The present invention is directed to a therapy method and apparatus for treatment of a patient with focused acoustic waves of the type having a source of focused acoustic waves, means for receiving echoes of the acoustic waves reflected from a subject to be treated, and means for switching the apparatus from a locating to a therapy mode.

2. Description of the Prior Art

Non-invasive acoustic therapy systems are utilized, for example, for the disintegration of calculi (lithotripsy), for treating tumor pathologies (hyperthermia) or for treating bone conditions (osteorestoration). The received, reflected parts of the acoustic waves are employed for locating the region to be treated. For example, the chronological relation between the generation of the acoustic waves and the reception of their reflected parts is utilized to judge whether the region to be treated is located in the focus of the acoustic waves. When the chronological allocation indicates a position of the region to be treated outside the focus, the source of acoustic waves and the subject to be treated are displaced relative to one another such that a chronological allocation is achieved that indicates the region to be treated is in the focus of the acoustic waves.

German OS 27 22 252 discloses such a therapy system for use with the disintegration of calculi on the basis of shockwaves. In this therapy system, reduced-energy shockwaves are generated during locating mode. Damage to the tissue surrounding the calculus to be disintegrated during the locating procedure is prevented in this way. The parts of the shockwaves reflected from the subject to be treated are received with a plurality of broadband pressure sensors. The output signals of the pressure sensors, however, do not allow the region to be treated, i.e. the calculus, to be exactly positioned in the focus of the acoustic waves under all circumstances.

SUMMARY OF THE INVENTION

It is an object of the present invention to provide a therapy system of the type initially described wherein a more exact positioning of the region to be treated in the focus of the acoustic waves is possible.

This object is achieved in accordance with the principles of the present invention in a therapy apparatus for treatment with focused acoustic waves having a shockwave unit as a source of focused acoustic waves, means for receiving parts of the acoustic waves reflected from a subject to be acoustically irradiated, means for switching the apparatus from a therapy mode to a locating mode, and means for varying the oscillatory frequency of the generated acoustic waves dependent on whether the apparatus is switched to the therapy or to the locating mode. In the therapy apparatus of the invention, thus, it is possible to match the oscillatory frequency of the generated acoustic waves originally to the requirements of the therapy mode and optimally to the requirements of the locating mode. This represents a considerable advantage over known systems because first, the size of the focus region of the acoustic waves, and second, the attenuation that the acoustic waves experience in the subject to be treated, are dependent on the frequency of the acoustic waves. For reducing the treatment duration and for subjecting a patient to an optimally low dose of acoustic energy, it is advantageous in for the therapy mode for the size of the focus region to approach that of the region to be treated as closely as possible, and for the attenuation of the acoustic waves to be optimally low in the subject being treated. During the locating mode, a higher attenuation of the acoustic waves does not inherently represent a problem, as long as it is assured that their reflected parts reach the means for reception with adequate amplitude. The focus zone during the locating mode should, however, be optimally small, since the topical resolution increases as the size of the focus zone decreases.

In a preferred embodiment of the invention, the oscillatory frequency of the acoustic waves is higher in the locating mode than in the therapy mode. The therapy mode is especially effective as a consequence of the larger focus zone and of the low attenuation of the acoustic waves in the subject to be treated. In the case of the locating mode, wherein the attenuation of the acoustic waves in the subject to be treated is of secondary significance, a small focus zone is achieved resulting in a high precision of the locating procedure.

In another embodiment of the invention the source has a single, electrical generator allocated to it with which it can be driven to generate acoustic waves, the generator—when the therapy apparatus is switched to the locating mode—driving the source for generating acoustic waves at an oscillatory frequency which is different from the oscillatory frequency during the therapy mode. Only one generator is thus required, making the system more economical. In certain instances, however, it may be desired that not only the oscillatory frequency but also other acoustic characteristics of the acoustic waves, for example, their amplitude, should deviate greatly in the locating mode from their values in the therapy mode. In a further embodiment of the invention for such instances, the source has two electrical generators allocated to it, one driving the source during the therapy mode and the other driving the source during the locating mode, the generator for the therapy mode and the generator for the locating mode driving the source for generating acoustic waves with respectively different frequencies and, if desired different amplitudes.

If the means for reception contain a piezoelectrically activated element, this element can be activated for the emission of acoustic locating waves whose frequency is higher than the acoustic waves generated by the source during therapy mode, in addition to the normal function of the means for reception of receiving parts of the locating waves reflected from the subject. This makes it possible to employ locating waves whose frequency and other acoustic characteristics can be selected entirely independently of the conditions of the therapy wave source.

In another preferred version of the invention, the source of acoustic waves is an electromagnetic pressure pulse source that can be charged with a pulse-like current by a capacitor discharge for generating a pressure pulse, with the effective capacitance differing for the therapy mode and for the locating mode.

DESCRIPTION OF THE PREFERRED EMBODIMENTS

The invention is shown in the figures in the exemplary form of therapy equipment for non-invasive disintegration of calculi, the sources of acoustic waves therein being acoustic pressure pulse sources fashioned as shockwave units.

Figure 1:
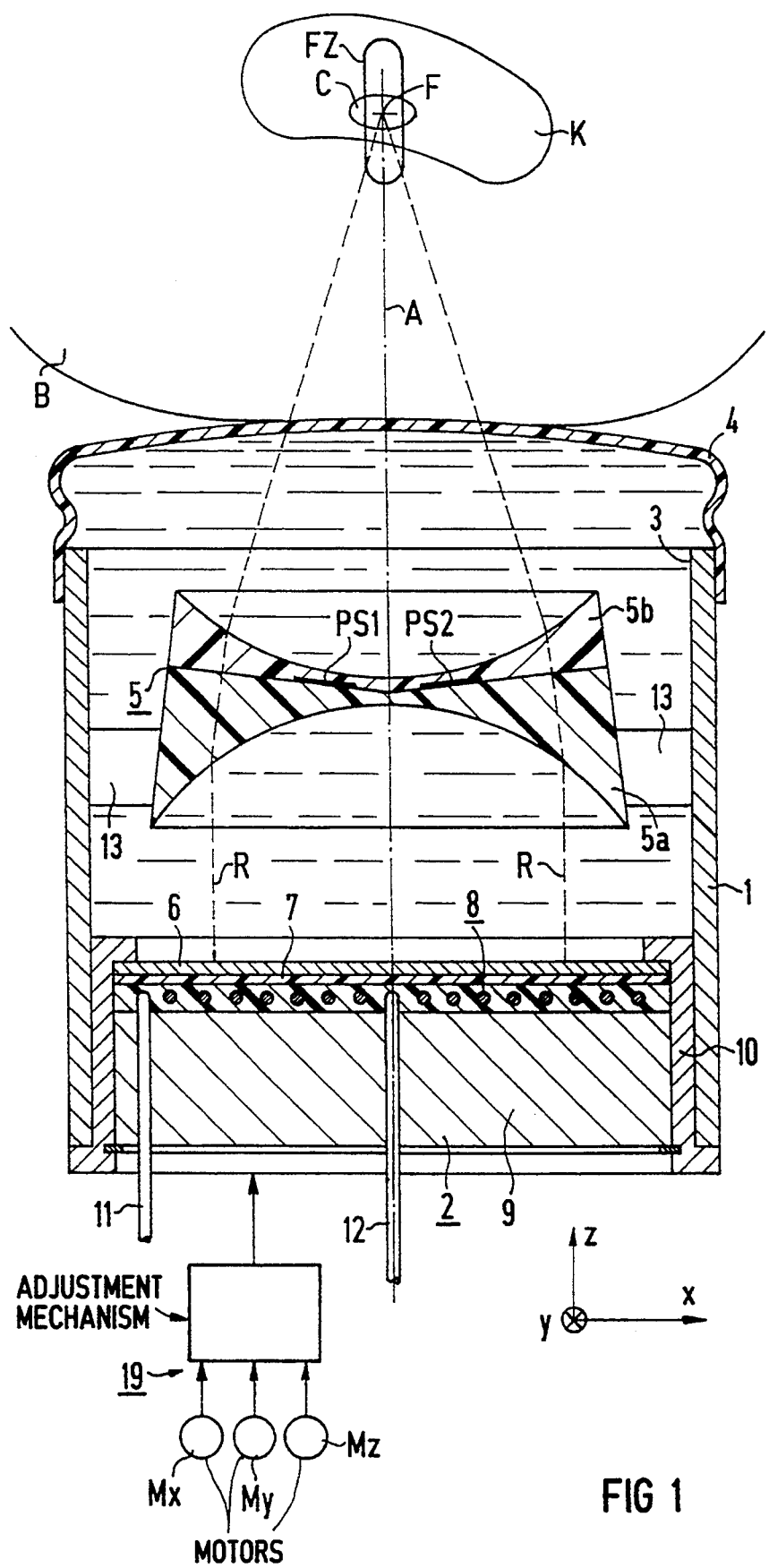
FIG. 1 is a longitudinal section through a shockwave unit of a therapy apparatus constructed in accordance with the principles of the present invention, shown in a schematic illustration.

As shown in FIG. 1, a shockwave unit for the therapy apparatus of the invention has a tubular housing 1 with a shockwave generator generally referenced 2 disposed at one end. An exit opening 3 for the pressure pulses emanating from the shockwave generator 2 is situated at the other end of the housing 1, this being closed with a flexible sack 4. The space surrounded by the shockwave generator 2, the housing 1 and the flexible sack 4 contains water, for example, serving as liquid acoustic propagation medium for the pressure pulses emanating from the shockwave generator 2. These pressure pulses gradually intensify along their propagation path to form shockwaves as a consequence of the non-linear compression properties of the propagation medium. The term "shockwave" shall always be employed herein for simplicity, regardless of whether a pressure pulse has in fact already intensified to form a shockwave.

An acoustic positive lens 5 arranged in the propagation medium is provided for focusing the shockwaves emanating from the shockwave generator 2. This acoustic positive lens 5 focuses the shockwaves onto a focus zone FZ whose center is referenced F and which lies on an acoustic axis A of the shockwave unit, which coincides with the center axis of the shockwave unit. The contour of the focus zone FZ shown in FIG. 1 surrounds that region within which the pressure of the shockwaves is at least equal to half the maximum pressure occurring in the focus zone FZ (−6 dB zone).

The shockwave unit can be pressed against the schematically indicated body B of a patient for acoustic coupling with the flexible sack 4. The shockwave unit is thereby aligned such that a calculus C situated in the body B of the patient and to be disintegrated, for example a kidney stone K, is located in the focus zone FZ. As described below, this occurs by receiving and evaluating the parts of the shockwaves generated with the shockwave generator 2 that are reflected at the calculus C to be disintegrated. The reflected parts thereof are spherical diffracted waves. In addition, an x-ray locating means (not shown) or an ultrasound locating means (likewise not shown) that preferably contains an ultrasound sector applicator can be provided in a known way.

An electromagnetic shockwave generator that is disclosed in greater detail in U.S. Pat. No. 4,674,505 can be used as the shockwave generator 2. The shockwave generator 2 includes a circular disc-shaped, planar membrane 6 composed of an electrically conductive material having one side directly adjacent to the water enclosed in the shockwave unit. A planar, surface coil generally referenced 8 is helically wound and is applied on a coil carrier 9 composed of an electrically insulating material. The planar surface coil 8 is arranged opposite the other side of the membrane 6 with an insulating foil 7 interposed therebetween. An electrically insulating casting compound is situated between the helically proceeding turns of the surface coil 8. These components of the shockwave generator 2 are accepted in axially non-dislocatable fashion in the bore of a mounting ring 10, which is in turn held in an axially non-dislocatable fashion in the bore of the housing 1.

The surface coil 8 has two terminals 11 and 12 via which it is connected to a high-voltage pulse generator (not shown in FIG. 1 ). The generator charges the surface coil 8 with high-voltage pulses. When the surface coil 8 is charged with a high-voltage pulse, this results in a magnetic field arising extremely quickly. As a result, a current is induced in the membrane 6, in a direction opposite the current in the surface coil 8, and consequently an opposing magnetic field is generated causing the membrane 6 to suddenly move away from the surface coil 8. A planar shockwave is introduced into the water situated in the shockwave unit as a result.

The positive lens 5 provided for the purpose of focusing the planar shockwaves is a biconcave lens that is substantially dynamically balanced with respect to the acoustic axis A and which is composed of a material, for example polystyrol, in which the speed of sound is higher than in the water provided as the acoustic propagation medium. The positive lens 5 is secured in the bore of the housing 1 with a plurality of supporting arms 13, two of these being visible in FIG. 1. The positive lens 5 is composed of two lens parts 5a and 5b. The partition between the two lens parts 5a and 5b is a surface which, except for its inclination relative to the acoustic axis A is otherwise planar, and which is rotationally symmetrical relative to the acoustic axis A. This surface is a conical surface in the exemplary embodiment. Three pressure sensors PS1, PS2 and PS3 (shown in FIG. 2) are applied onto the concave, conical separating plane of the lens part 5a. These pressure sensors are piezoelectrically activated polyvinylidene fluoride (PVDF) foils provided with electrodes that, as viewed in the direction of the acoustic axis A, respectively have the shape of an annulus sector extending just under 120°. The annulus sectors are congruent and the pressure sensors PS1, PS2 and PS3 are arranged such that their centers of curvature lie on the acoustic axis A. Via signal lines that are not shown in FIG. 1, the pressure sensors PS1, PS2 and PS3 are in communication with an evaluation electronics which is likewise not shown in FIG. 1. As a consequence of the fashioning of the separating plane between the lens parts 5a and 5b as a planar surface (except for its inclination), the pressure sensors PS1, PS2 and PS3 can be unproblematically applied thereto, particularly without the risk of creating folds. The two lens parts 5a and 5b are glued to one another with a suitable adhesive. Since the thickness of the pressure sensors lies on the order of magnitude of 30

μm, the adhesive is easily capable of bridging the gap present between the two lens parts 5a and 5b outside the pressure sensors PS1, PS2 and PS3.

An adjustment mechanism 19 includes electric motors Mx, My and Mz schematically indicated in FIG. 1, is allocated to the shockwave unit. The adjustment mechanism 19 which, for example, contains gearings the like in a known way, serves the purpose of adjusting the shockwave unit in the directions of the axes of the rectangular spatial coordinate system shown in FIGS. 1 and 2. The motor Mx is responsible for the adjustment in the direction of the x-axis, the motor My is responsible for the adjustment in the direction of the y-axis, and the motor Mz is responsible for the adjustment in the direction of the z-axis of the coordinate system. The z-axis, moreover, corresponds to the acoustic axis A proceeding through the center F of the focus zone FZ. The y-axis proceeds parallel to the angle bisector of the pressure sensor PS3.

Figure 2:
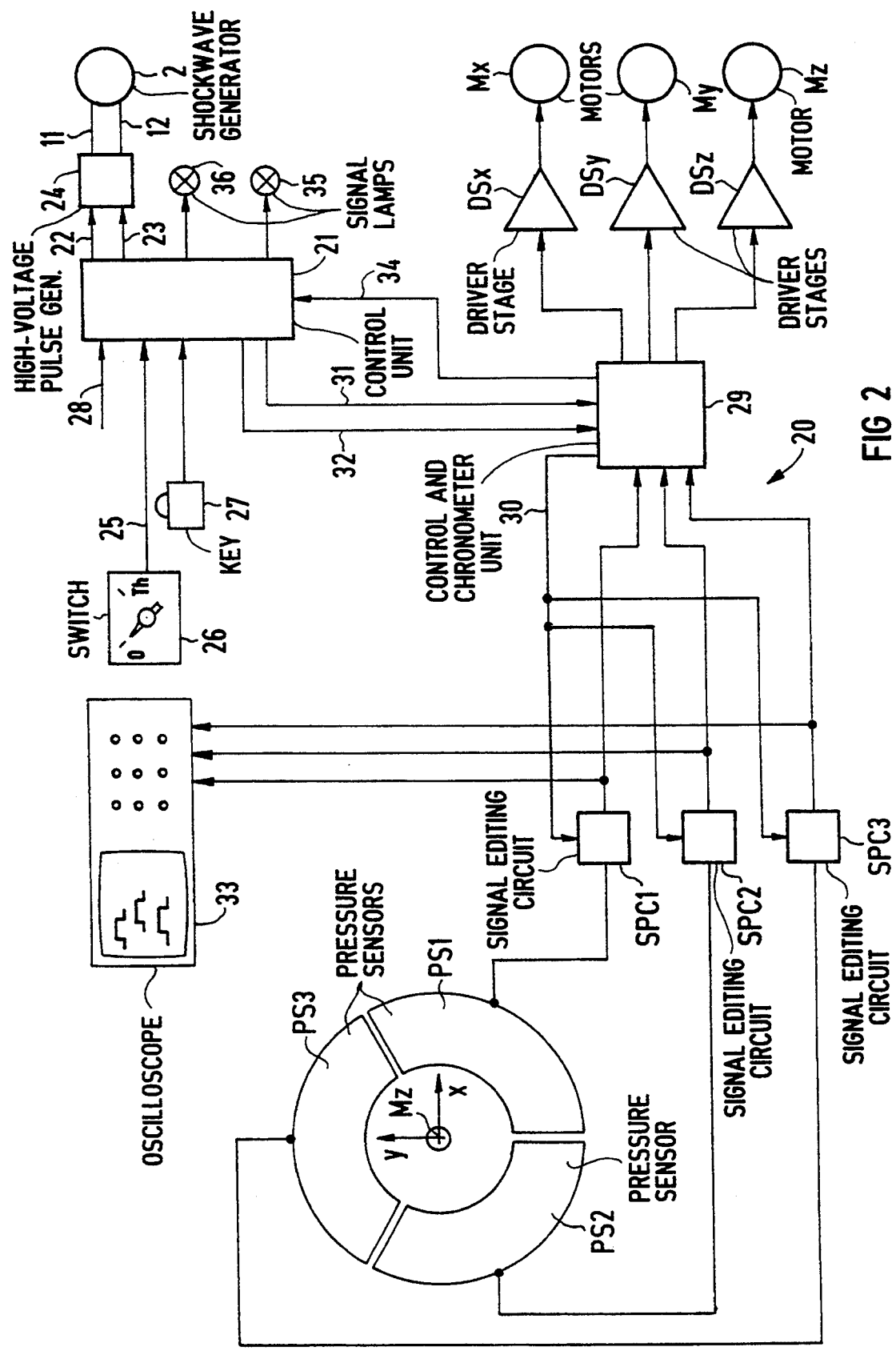
FIG. 2 is a front view of the pressure sensor arrangement of the shockwave unit of FIG. 1 and a schematic illustration of a block circuit diagram of the therapy apparatus of the invention.

The pressure sensors PS1, PS2 and PS3 are connected to an evaluation and drive electronics 20 which is in turn connected to a control unit 21. Via two control lines 22 and 23, a high-voltage pulse generator 24 is in communication with the control unit 21, the schematically indicated shockwave generator 2 being connected to the high-voltage pulse generator 24 via the terminals 11 and 12. A switch 26, with which the therapy apparatus can be selectively switched into the locating mode or into the therapy mode is connected to the control unit 21 via a line 25. In FIG. 2, the switch 26 assumes its position referenced O for the locating mode. Its other position, which corresponds to the therapy mode, is referenced Th. When the switch 26 assumes its position for the locating mode, the control unit 21—via the control line 22—initializes the high-voltage pulse generator 24 to generate shockwaves whose fundamental wave has an oscillatory frequency that is higher a the factor of 5 through 10 than the oscillatory frequency of the fundamental wave of the shockwaves generated during therapy mode. The amplitude of the shockwaves generated in the locating mode, moreover, is greatly reduced in comparison to the amplitude during therapy mode, to such an extent that the shockwaves still have a peak pressure on the order of magnitude of a few bar in the region of the calculus. During therapy mode the peak pressures are, for example, on the order of magnitude of a few 100 bar. The frequency of the fundamental wave of the shockwaves generated during the therapy mode is, for example, on the order of magnitude of 70 kHz through 300 kHz. The corresponding value for the locating mode then, for example, is on the order of magnitude of 1 MHz. Of course, the shockwaves also contain higher-frequency harmonics during therapy as well as in the locating mode since shockwaves are extremely broadband signals.

In the locating mode, the control unit 21 initializes the high-voltage pulse generator 24 to separate shockwaves having a repetition rate on the order of magnitude of a few Hz through a few 100 Hz. The control unit 21 supplies the corresponding trigger pulses to the high-voltage pulse generator 24 via the control line 23. In the therapy mode, there is the optional possibility to trigger individual shockwaves by actuation of a key 27 or to supply trigger pulses that are derived from a periodic body function of the patient to be treated, for example from the respiratory and/or heart activity of the patient, to the control unit via a trigger line 28 in a known way.

The evaluation and drive circuit 20 includes signal editing circuits SBC1 through SBC3 to which the output signals of the pressure sensors PS1 through PS3 are supplied. The signal editing circuits SPC1 through SPC3 are controlled via a control line 30 by a control and chronometer unit 29 such that their inputs are blocked for a time after the generation of a shockwave, this time at least corresponding to the transit time of the shockwave from the shockwave generator 2 through the positive lens 5 and not being significantly longer than the transit time of the shockwave from the shockwave generator 2 to the calculus C to be disintegrated. The control and chronometer unit 29 receives the clock signals required for this purpose from the control means 21 via a line 31. Only those parts of the output signals of the pressure sensors PS1 through PS3 that represent a spherical diffraction wave emanating from the calculus C to be disintegrated after the calculus is charged with a shockwave can thus proceed into the signal editing circuits SPC1 through SPC3. By means of, for example, a Schmitt trigger with a following monoflop, these signal parts are converted into square-wave pulses having a defined duration in the identical signal editing circuits SPC1 through SPC3, with the duration of the square-wave pulses being greater than the overall duration of the diffraction wave. This means that each diffraction wave can trigger the monoflops contained in the signal editing circuits SPC1 through SPC3 only a single time. The aforementioned square-wave pulses are supplied to the control and chronometer unit 29. The unit 29 measures, first, the chronological duration by which the leading edges of the square-wave pulses from the signal editing circuits SPC1 and SPC2 are offset relative to one another. When there is a chronological offset, the control and chronometer unit 29 drives the motor Mx of the adjustment mechanism 19 via the driver stage DSx that the shockwave unit is brought into a position by being adjusted in the direction of the x-axis such that the chronological duration is equal to zero, the transit time difference of the parts of the diffraction wave proceeding to the pressure sensors PS1 and PS2 thus being likewise equal to zero. This is the case when the calculus C to be disintegrated lies in a plane containing the y-axis and x-axis.

Following thereupon, the chronological duration between the leading edges of the square-wave signals that derive from the signal editing circuit SPC3 and from the signal editing circuit SPC1 or SPC2 is measured. If this chronological duration differs from zero, the control and chronometer unit 29 drives the motor My of the adjustment mechanism 19 via the driver stage DSy such that this motor My adjusts the shockwave unit in the direction of the y-axis into a position so that the chronological difference is equal to zero. This is the case when the transit time difference of the parts of the diffraction wave proceeding to the pressure sensor PS3 and to the pressure sensor PS1 or PS2 is equal to zero, and the calculus C to be disintegrated thus lies on the acoustic axis A. There is now no longer any chronological offset whatsoever between the square-wave pulses from the signal editing circuits SPC1 through SPC3.

Finally, the control and chronometer unit 29 measures the chronological duration that elapses between the activation of the shockwave generator 2 to generate a shockwave (a signal is supplied at the time of activation to the control and chronometer unit 29 by the control unit 21 via a line 32) and the arrival of the leading edge of the square-wave pulse formed from the output signal of one of the pressure sensors PS1 through PS3, for example the pressure sensor PS1. The control and chronometer unit 29 identifies the chronological difference between the chronological duration measured in this way and a value stored in the control and chronometer unit 29, this value corresponding to the sum of the transit times of the shockwaves from the shockwave generator 2 to the calculus C to be disintegrated and the transit time of the diffraction wave from the calculus C to be disintegrated to the pressure sensor PS1 when the calculus to be disintegrated is exactly situated in the focus zone. When this chronological difference differs from zero, the control and chronometer unit 29 controls the motor Mz of the adjustment mechanism 19 via the driver stage DSz such that the motor Mz displaces the shockwave unit in the direction of the z-axis until the said chronological difference is equal to zero.

When driving the motors Mx and My, the control and chronometer unit 29 proceeds such that it first sets the former chronological duration to zero on the basis of a step-by-step drive of the motor Mx with a step width of, for example, 1 millimeter following every shockwave. In a corresponding fashion, the control and chronometer means 29 drives the motor My step-by-step until the second-cited chronological duration is zero. The control and chronometer means 29 determines the adjustment direction that is required by identifying that pressure sensor PS1 through PS3 participating in the adjustment event to which the first-arriving pulse belongs. The adjustment in z-direction ensues analogously step-by-step, with the adjustment direction again being derived from the operational sign of the chronological difference identified in the above way.

In order to enable an optical supervision of the alignment of the shockwave unit relative to the calculus z to be disintegrated, the output signals of the signal editing circuits SPC1 through SPC3 are supplied to a multichannel oscilloscope 33 at which they are displayed vertically above one another in correct phase relation. An exact alignment is established when the leading edges of all square-wave pulses lie on a single vertical line.

When the correct alignment of the shockwave unit relative to the calculus C to be disintegrated has been completed in the above-described way, the control and chronometer means 29 transmits a corresponding signal via the line 34 to the control unit 21, which, in response thereto, generates a signal indicating the end of the locating procedure. In the case of the exemplary embodiment which has been set forth, this is an optical signal, i.e. a signal lamp 35 having, for example, a green color which is illuminated.

The therapy apparatus can now be switched from the locating to the therapy mode with the switch 26. In therapy mode, the control unit 21 controls the high-voltage pulse generator 24 via line 22 such that it generates shockwaves having an amplitude suitable for the therapy mode, whereby the frequency of the fundamental of the shockwave is also reduced in comparison to the locating mode. The output of shockwaves in the therapy mode, as already set forth, ensues when the key 27 is actuated or when a trigger pulse proceeds to the control unit 21 via the trigger line 28.

An evaluation of the output signals of the pressure sensors PS1 and PS2 also ensues during therapy mode, these output signals representing the diffraction waves that arise as a consequence of charging the calculus C to be disintegrated with the shockwaves generated during therapy mode. As a consequence of the frequency of the fundamental of the shockwaves generated during the therapy mode being diminished in comparison to locating mode, the same topical resolution as in the locating mode is not achieved, however, a continuous supervision with adequate precision is possible to monitor whether the shockwave unit is still aligned in the required way relative to the calculus C to be disintegrated. The signal lamp 35 remains activated as long as this is true. When, by contrast, the output signals of the pressure sensors PS1 through PS3 indicate that the correct alignment of the shockwave unit relative to the calculus C to be disintegrated is no longer present, the control and chronometer unit 29 forwards a corresponding signal via the line 34 to the control unit 21 which subsequently deactivates the signal lamp 35. Simultaneously, the control unit 21 ignores actuations of the key 27, or respectively ignores trigger pulses arriving via the trigger line 28. Only when the therapy apparatus has again been switched to locating mode with the switch 26 and the alignment of the shockwave unit relative to the calculus C to be disintegrated has been corrected is a reassumption of the therapy mode enabled after a corresponding actuation of the switch 26 back to the therapy mode.

If one of the pressure sensors PSC1 through PSC3 fails, the control and chronometer means 29 likewise forwards a corresponding signal via the line 34 to the control unit 21 which then activates a further signal lamp 36 that chromatically differs from the signal lamp 35.

Although the possibility exists of undertaking the locating of the calculus C to be disintegrated in the described way exclusively on the basis of the output signals of the pressure sensors PS1 through PS3, it can be expedient to undertake a pre-locating with the assistance of an x-ray and/or ultrasound locating system and only to undertake the required, fine corrections in the described way on the basis of the output signals of the pressure sensors PS1 through PS3.

Figure 3:
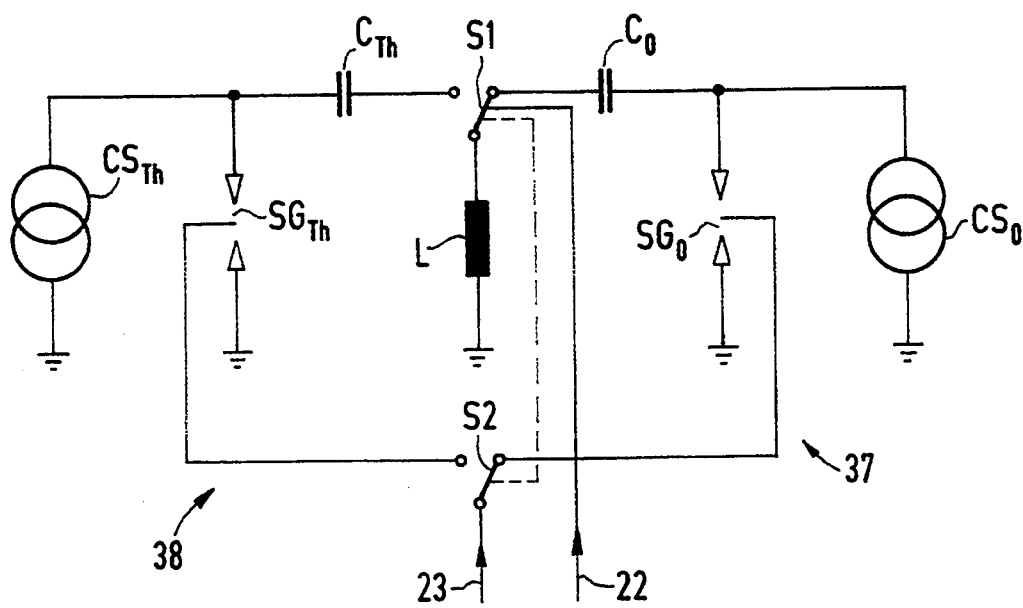
FIG. 3 is a schematic circuit diagram of a high-voltage pulse generator for the therapy apparatus of FIGS. 1 and 2.

FIG. 3 shows the circuit of the high-voltage pulse generator 24 in greater detail. The shockwave generator 2 is symbolized by the inductance L of its surface coil 8 having one end at ground. Via a suitable switch element S1 that is actuated by the control unit 21 via the line 22 dependent on whether the locating or the therapy mode is selected with the switch 26, the other end of the surface coil 8 can be connected to a capacitor $C_O$, having a smaller capacitance that is effective during locating mode, or to a capacitor $C_{Th}$, having a higher capacitance that is effective in therapy mode. A respective charging current source $CS_O$ or $CS_{Th}$ is allocated to the capacitors $C_O$ and $C_{Th}$. Two triggerable spark gaps $SG_O$ and $SG_{Th}$ have primary electrodes respectively connected to the charging current sources $CS_O$ or $CS_{Th}$, and each have a further primary electrode connected to ground. Dependent on the position of the switch element S1 the capacitor $C_O$ or $C_{Ch}$ will be discharged by the associated sparkgap $SG_O$ or $SG_{th}$ to generate a shockwave on the basis of the inductance L (i.e., the surface coil 8) of the shockwave generator 2. Dependent on whether the locating or the therapy mode has been selected, the auxiliary electrode of the corresponding spark gap $SG_O$ or $SG_{Th}$ is connected to the control line 23 from the control unit 21 in the required way with switch element S2 coupled to the switch element S1. Via the control line 23, the auxiliary electrode of the respective spark gap $SG_O$ or $SG_{Th}$ is supplied with trigger pulses in the required way, a trigger pulse causing the triggering (firing) of the corresponding spark gap $SG_O$ or $SG_{Th}$. The high-voltage pulse generator 24 thus contains two generator devices generally referenced 37 and 38 respectively used for the locating or for the therapy mode, that are independent of one another, whereby the former is formed by the elements $CS_O$, $C_O$ and $SG_O$ and the latter is formed by the elements $CS_{Th}$, $C_{Th}$ and $SG_{Th}$.

For a given electromagnetic shockwave generator, the frequency of the fundamental wave of the generated shockwaves increases with a decrease of the capacitance of the capacitor discharged to produce the current pulses for generating the shockwaves, and the amplitude of the shockwaves becomes lower as the capacitance of the capacitor decreases. It is thus clear that shockwaves are generated in the locating mode having an intensity which is lower and a fundamental wave frequency which is higher than is the case in therapy mode, by means of the high-voltage pulse generator of FIG. 3. A further reduction in the amplitude of the shockwaves generated in the locating mode is possible when the capacitor $C_O$ is charged to a lower voltage by the current source $CS_O$ than is the capacitor $C_{Th}$ with the current source $CS_{Th}$.

Figure 4:
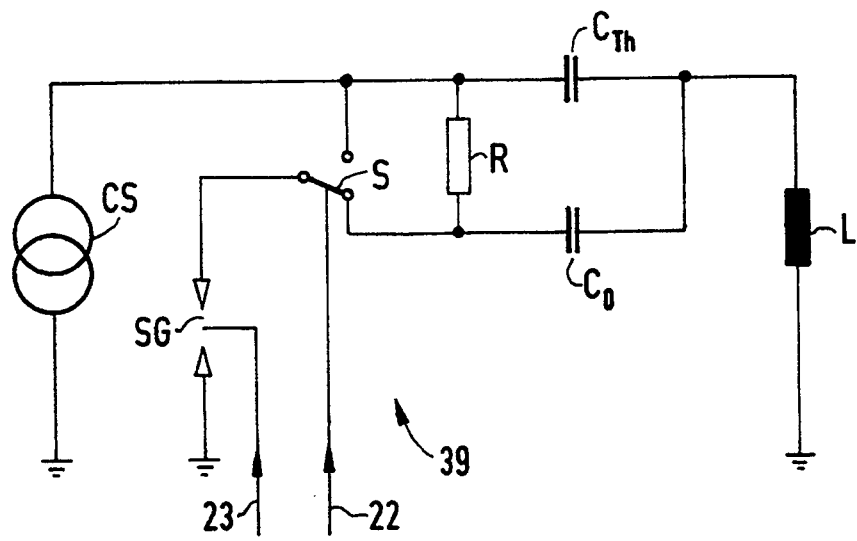
FIG. 4 is a further version of the therapy apparatus of the invention shown in an illustration analogous to FIG. 3.

FIG. 4 shows another embodiment of a therapy apparatus of the invention that differs from the above-described embodiment only in view of the fashioning of the high-voltage pulse generator 24 for the shockwave unit 2. According to FIG. 4, a single charging current source CS is provided, the capacitor $C_{Th}$ effective in the therapy mode having one terminal connected thereto. The other terminal of the capacitor $C_{Th}$ is connected to a terminal of the surface coil 8 (illustrated as an inductance L in FIG. 4) of the shockwave generator 2 whose other terminal is at ground. The capacitor $C_{Th}$ is connected in parallel with a series circuit formed by the capacitor $C_O$ responsible for the locating mode and a resistor R. Thus the capacitors $C_{Th}$ and $C_O$ can be simultaneously charged with the charging current source CS. Dependent on the repetition rate with which the shockwaves can be generated in the locating mode, the resistor R has a resistance that is optimally high. Further, a triggerable spark gap SG is provided having one primary electrode at ground and another primary electrode which can be selectively connected to one or the other terminal of the resistor R via a suitable switch S, actuated as required by the control unit 21 via the control line 22. The auxiliary electrode of the spark gap SG is in communication with the control unit 21 via the control line 23. During the therapy mode, the switch S assumes that position causing the primary electrode of the spark gap SG that is not connected to ground to be connected to that end of the resistor R that is connected to the capacitor $C_{Th}$. During the locating mode, by contrast, the switch S assumes the other position wherein the aforementioned primary electrode of the spark gap SG is connected to the other end of the resistor R that is in turn connected to the capacitor $C_O$. Thus only one capacitor $C_{Th}$ or $C_O$ discharges both in the therapy mode as well as in locating mode when the spark gap SG is triggered. The capacitor $C_O$ or $C_{Th}$ responsible for the other operating mode discharges to only an insignificant degree as a consequence of the series resistor R.

Since the high-voltage pulse generator of FIG. 4 contains only a single generator 39 for the locating and therapy modes which is formed by the elements CS, $C_O$, $C_{Th}$, SG and S, the shockwaves respectively generated in the two operating modes differ only slightly in view of their amplitude under certain circumstances. The high-voltage generator of FIG. 4 can then only be utilized in therapy equipment wherein the alignment of the shockwave unit relative to the calculus C to be disintegrated ensues on the basis of an x-ray and/or ultrasound locating system and the locating on the basis of the reflected parts of the shockwaves generated in the locating mode is utilized only for the fine alignment of the shockwave unit. Otherwise, there would be risk of damage to healthy tissue during locating mode because of the relatively high amplitude of the shockwaves generated in the locating mode. A further difference compared to the embodiment of FIG. 3 is that, if the evaluation of the output signals of the pressure sensors SP1 through SP3 during the therapy mode shows that the correct alignment of the shockwave unit relative to the calculus C to be disintegrated is no longer established, a return into the therapy mode is only possible after a re-alignment of the shockwave unit relative to the calculus C to be disintegrated has been undertaken with the x-ray and/or ultrasound locating system. The embodiment of FIG. 4 nonetheless offers the advantage that only one charging current source and only one spark gap are required.

The employment of spark gaps SG, $SG_O$ and $SG_{Th}$ as high-voltage switches in the high-voltage pulse generators according to FIGS. 3 and 4 is only by way of example. Other switch elements can alternatively be employed which are capable of handling the output voltages of the charging current sources CS, $CS_O$ and $CS_{Th}$ which, in the case of the charging current sources CS and $CS_{Th}$, can be on the order of magnitude of 10 through 20 kV and above. Since the voltage supplied by the charging current source $CS_O$ can clearly fall below this value, there is the possibility of employing suitable semiconductor switches instead of the spark gap $SG_O$.

Figure 5:
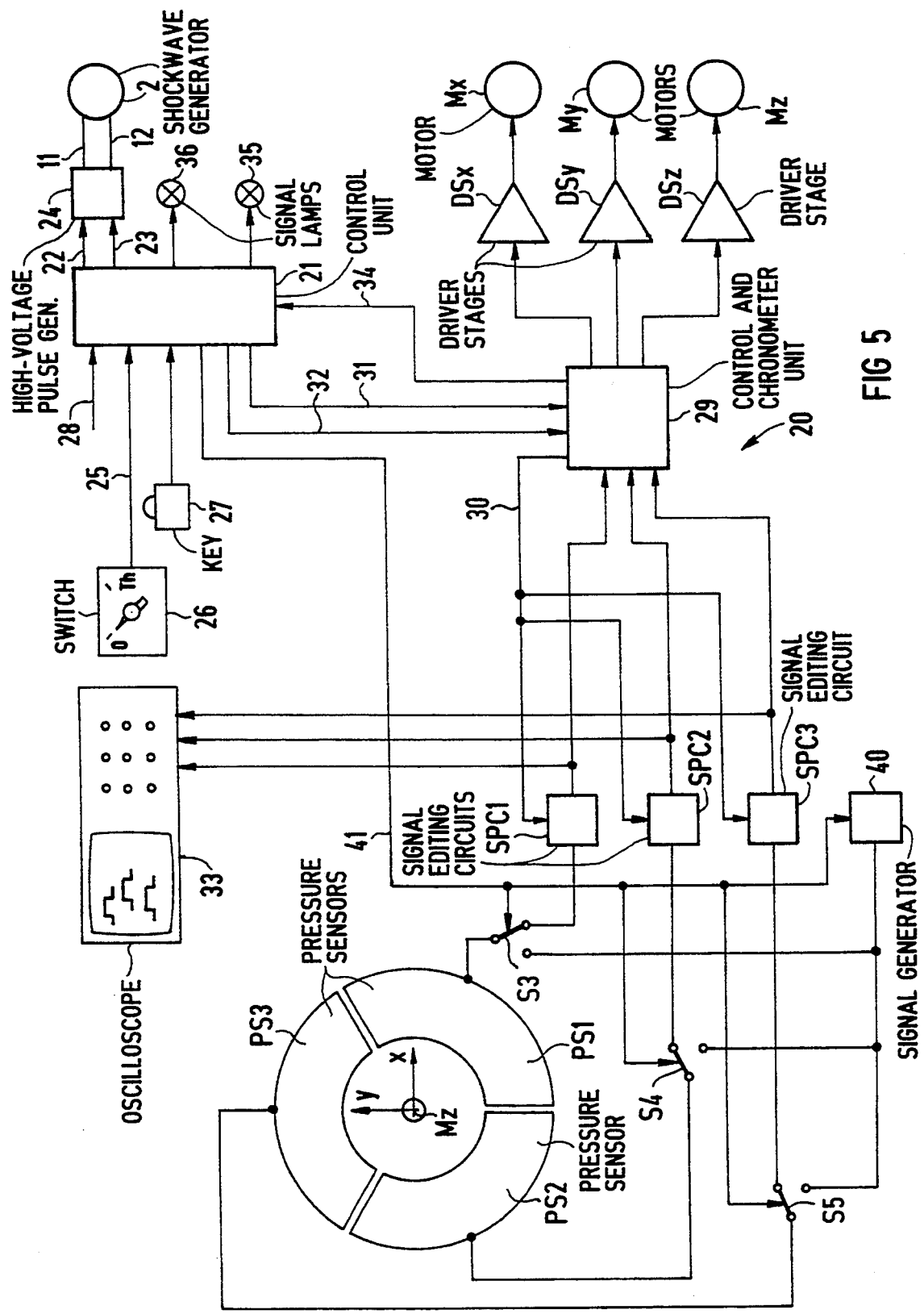
FIG. 5 is a further embodiment of the invention shown in an illustration analogous to FIG. 2.

FIG. 5 shows an exemplary embodiment that differs from that of FIGS. 1 through 3 in that switches S3 through S5 are inserted into the lines connecting the pressure sensors PS1 through PS3 to the evaluation and drive electronics 20, via which switches the pressure sensors PS1 through PS3 can be selectively connected to the signal editing circuits SPC1 through SPC3 or to a generator 40. The generator 40 drives the PVDF foils contained in the pressure sensors PS1 through PS3 to generate acoustic locating waves. To this end, the control unit 21 actuates the switches S1 through S3 via a control line 41 such that the pressure sensors PS1 through PS3 are connected to the generator 40, which is likewise driven via the control line 41 to generate an electrical signal output. This output proceeds through the pressure sensors PS1 through PS3 and drives elements piezoelectrically to generate the acoustic locating waves. After a sufficient time to guarantee that the electrical output signals of the pressure sensors PS1 through PS3 corresponding to the parts of the locating waves reflected from the body of the patient received by the pressure sensors PS1 through PS3 can proceed to the evaluation and drive electronics 20, the control unit 21 switches the switches S1 through S3 to their position shown in FIG. 5 wherein the pressure sensors PS1 through PS3 are connected to the evaluation and drive electronics 20.

The evaluation of the output signals of the pressure sensors PS1 through PS3 ensues analogously to the fashion set forth in conjunction with the exemplary embodiment of FIGS. 1 through 3.

The generation of the locating waves, for example, can ensue in such a way that the generator 40 charges the pressure sensors PS1 through PS3 with a current pulse. The locating waves are then acoustic pressure pulses. There is the also the possibility of the generator 40 driving the pressure sensors PS1 through PS3 to generate the locating waves with a pulse-like or burst-like sinusoidal signal, whereby the sinusoidal signal then extends over half a period or over a whole multiple of half a period. The locating waves are then essentially sinusoidal acoustic waves. In any case, the frequency of the locating waves is higher than the frequency of the fundamental wave of the shockwaves that the shockwave generator 2 emits during therapy mode. The amplitude of the locating waves is lower than that of the shockwaves generated in the therapy mode, and possibly lower than that of the shockwaves generated in the locating mode.

The shockwave generator 2 in the exemplary embodiment of FIG. 5 can also be activated in the locating mode in the way set forth in conjunction with the exemplary embodiment of FIGS. 1 through 3. The activation of the pressure sensors PS1 through PS3 to generate locating waves can ensue alternatively, by means of a corresponding operating element allocated to the control unit 21, not shown separately in FIG. 5. Preferably, moreover, the frequency of the locating waves generated with the pressure sensors PS1 through PS3 is higher than the frequency of the fundamental wave of the shockwaves generated by the shockwave generator 2 in the locating mode. Further, the control unit 21 will include an operating element, not shown separately in FIG. 5, which is actuatable to cause the switches S1 through S3 and the generator 40 to be driven in such a way during the therapy mode that the pressure sensors PS1 through PS3 are driven to generate locating waves between successive shockwaves generated with the shockwave generator 2. The output signals of the pressure sensors PS1 through PS3 representing reflected parts of the locating waves are interpreted by the evaluation and drive electronics 20 before the output of the next shockwave, and a drive of one or more of the motors Mx through Mz ensues as warranted. The emission of locating waves during therapy mode, moreover, can ensue after every individual shockwave generated with the shockwave generator 2 or can ensue after a selected number of shockwaves generated by the shockwave generator 2.

Because the diffraction waves emanating from the calculus in the exemplary embodiments are spherical waves, the aperture angle of the separating line between the two lens parts 5a and 5b is selected such that this line in the region wherein the pressure sensors PS1 through PS3 are arranged represents at least an approximation of a surface for which the maximum transit time differences that can arise between different locations of the pressure sensors PS1 through PS3 and the center F of the focus zone FZ are minimized or are equal to zero. Thus, only insignificant broadening of the output signals of the pressure sensors PS1 through PS3 occurs in the worst case without noteworthy influence on the obtainable topical resolution.

Other arrangements of pressure sensors are also possible. Thus, for example, the pressure sensors can be arranged (in a way not shown) between the positive lens 5 and the shockwave generator 2 in a plane that intersects the acoustic axis A at a right angle. There is also the possibility of placing the pressure sensors on that end face of the positive lens facing toward the focus zone FZ or on the end face of the positive lens facing toward the shockwave generator 2. There is also the possibility of arranging the pressure sensors in a planar surface that intersects the acoustic axis at a right angle and lies between the focus zone FZ and the acoustic positive lens 5 within the shockwave unit.

Three pressure sensors PS1 through PS3 are shown in the exemplary embodiments that have been set forth, however, more than three pressure sensors can be provided. In particular, it can be advantageous to provide a plurality of ring arrangements concentric to the acoustic axis A, each of which has three annular sector-shaped pressure sensors that are preferably arranged in a common plane or surface. *)

*) Focussing of the acoustic waves is not necessarily to be effected by means of acoustic lens means or by means of acoustic lens means alone, as in the case of described the examplary embodiments. Instead or additionally, for example, acoustic reflector means may be provided and/or a source of acoustic waves may be used which is shaped such, e.g. spherically, that the acoustic waves emanating from the source are already focussed.

The described exemplary embodiments are directed to therapy apparatus having an electrodynamic shockwave unit as the source of focused acoustic waves. Other acoustic pressure pulse generators can be provided instead. Moreover, there is also the possibility of providing a therapeutic ultrasound source as the source of acoustic waves, as employed, for example, for hyperthermia. Such a pressure pulse source does not emit the ultrasound waves as pressure pulses but as continuous sound in the therapy mode, and as locating pulses during the locating mode.

The described exemplary embodiments are directed to the employment of a therapy apparatus of the invention in conjunction with the disintegration of calculi. Of course, other applications such as, for example, the aforementioned hyperthermia and the treatment of bone conditions are also possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for treating a subject with acoustic waves comprising:

means for generating acoustic waves;

means for focussing said acoustic waves to a location in a subject;

means for receiving acoustic echoes of said acoustic waves reflected from said subject for use in maintaining said acoustic waves focussed at said location; and means for switching said means for generating said acoustic waves between a therapy mode for generating acoustic waves at a first oscillatory frequency and a locating mode for generating acoustic waves at a second oscillatory frequency.

2. An apparatus as claimed in claim 1 wherein said means for switching comprises means for switching said means for generating said acoustic waves between a therapy mode for generating acoustic waves at a first oscillatory frequency and a locating mode for generating acoustic waves at a second frequency with said second oscillatory frequency being higher than said first oscillatory frequency.

3. An apparatus as claimed in claim 1 wherein said means for generating acoustic waves comprises:
   a single acoustic wave source; and
   single electrical generator means for said source operable for driving said source in said therapy mode for generating said acoustic waves at said first oscillatory frequency and for driving said source in said locating mode for generating said acoustic waves at said second oscillatory frequency.

4. An apparatus as claimed in claim 1 wherein said means for generating acoustic waves comprises:
   a single source of acoustic waves;
   first electrical generator means for driving said source in said therapy mode at said first oscillatory frequency; and
   second electrical generator means for driving said source in said locating mode at said second oscillatory frequency.

5. An apparatus as claimed in claim 4 wherein said first and second electrical generator means each include means for respectively driving said source to generate acoustic waves of different amplitudes in said therapy mode and said locating mode.

6. An apparatus as claimed in claim 1 wherein said means for receiving acoustic echoes includes a piezoelectric element which generates electrical signals corresponding to said acoustic echoes incident thereon.

7. An apparatus as claimed in claim 6 further comprising means for driving said piezoelectric element in said therapy mode for generating acoustic waves having an oscillatory frequency which is higher than an oscillatory frequency of said acoustic waves generated by said means for generating acoustic waves in said therapy mode.

8. An apparatus as claimed in claim 1 wherein said means for generating acoustic waves comprises an electromagnetic pressure pulse source and means for driving said electromagnetic pressure pulse source.

9. An apparatus as claimed in claim 8 wherein said means for driving said electromagnetic pressure pulse source comprises a capacitance, means for charging and subsequently discharging said capacitance for supplying a drive signal to said electromagnetic pressure pulse source to generate a pressure pulse, and means for varying said capacitance between said therapy mode and said locating mode.

10. A method for treating a subject with acoustic waves comprising the steps of:
    generating acoustic waves;
    focussing said acoustic waves to a location in a subject;
    receiving acoustic echoes of said acoustic waves reflected from said subject for maintaining said acoustic waves focussed at said location; and
    switching generation of said acoustic waves between a therapy mode for generating acoustic waves at a first oscillatory frequency and a locating mode for generating acoustic waves at a second oscillatory frequency.

11. A method as claimed in claim 10 wherein the steps of switching is further defined by switching generation of said acoustic waves between a therapy mode for generating acoustic waves at a first oscillatory frequency and a locating mode for generating acoustic waves at a second oscillatory frequency with said second frequency being higher than said first oscillatory frequency.

12. A method as claimed in claim 10 wherein the steps of generating acoustic waves comprises:
    generating said acoustic waves from a single acoustic wave source; and
    operating a single electrical generator means for said source for driving said source in said therapy mode for generating said acoustic waves at said first oscillatory frequency and for driving said source in said locating mode for generating said acoustic waves at said second oscillatory frequency.

13. A method as claimed in claim 10 wherein the step of generating acoustic waves comprises:
    generating said acoustic waves from a single source of acoustic waves;
    driving said source with a first electrical generator means in said therapy mode at said first oscillatory frequency; and
    driving said source with a second electrical generator means in said locating mode at said second oscillatory frequency.

14. A method as claimed in claim 13 comprising the additional step of operating said first and second electrical generator means for respectively driving said source to generate acoustic waves of different amplitudes in said therapy mode and said locating mode.

15. A method as claimed in claim 10 wherein the step of receiving acoustic echoes is further defined by receiving acoustic echoes with a piezoelectric element which generates electrical signals corresponding to said acoustic echoes incident thereon.

16. A method as claimed in claim 15 comprising the additional steps of driving said piezoelectric element in said therapy mode for generating acoustic waves having an oscillatory frequency which is higher than an oscillatory frequency of said acoustic waves generated in said therapy mode.

17. A method as claimed in claim 10 wherein the steps of generating acoustic waves is further defined by driving an electromagnetic pressure pulse source.

18. A method as claimed in claim 17 wherein the steps of driving said electromagnetic pressure pulse source is further defined by charging and subsequently discharging a capacitance for supplying a drive signal to said electromagnetic pressure pulse source to generate a pressure pulse, and for varying said capacitance between said therapy mode and said locating mode.

19. An apparatus for treating a subject with acoustic waves comprising:
    means for generating acoustic waves having a shape for focussing said acoustic waves to a location in a subject;
    means for receiving acoustic echoes of said acoustic waves reflected from said subject for use in maintaining said acoustic waves focussed at said location; and
    means for switching said means for generating said acoustic waves between a therapy mode for generating acoustic waves at a first oscillatory frequency and a locating mode for generating acoustic waves at a second oscillatory frequency.

20. An apparatus as claimed in claim 1 wherein said means for switching comprises means for switching said means for generating said acoustic waves between a therapy mode for generating acoustic waves at a first oscillatory frequency and a locating mode for generating acoustic waves at a second oscillatory frequency with said second frequency being higher than said first oscillatory frequency.

* * * * *